United States Patent [19]
Esposito

[11] 4,332,613
[45] Jun. 1, 1982

[54] SOLUTIONS OF BROMOXYNIL AND IOXYNIL

[75] Inventor: James E. Esposito, Chalfont, Pa.

[73] Assignee: Union Carbide Corporation, Danbury, Conn.

[21] Appl. No.: 106,739

[22] Filed: Dec. 26, 1979

[51] Int. Cl.$^3$ .............................................. A01N 37/34
[52] U.S. Cl. .................................. 71/105; 71/DIG. 1
[58] Field of Search ..................... 71/105, DIG. 1, 118

[56] References Cited

U.S. PATENT DOCUMENTS

| | | | |
|---|---|---|---|
| 3,592,626 | 7/1971 | Heywood et al. | 71/105 |
| 3,830,642 | 8/1974 | Moon | 71/DIG. 1 |
| 3,986,862 | 10/1976 | Armstrong | 71/118 |
| 3,997,322 | 12/1976 | Ratledge | 71/DIG. 1 |
| 4,150,968 | 4/1979 | Young et al. | 71/DIG. 1 |
| 4,163,662 | 8/1979 | Baker, Jr. | 71/118 |

OTHER PUBLICATIONS

Veenstra et al., "Chemical Weed Control, etc." (1974), CA 87, No. 112858 p. (1977).
Ayres, "Control of Annual Broad–Leaved, etc." (1976), CA 87, No. 79519 d. (1977).
Sieberhein et al., "Importance and Control, etc." (1974), CA 83, No. 2084 t. (1975).

*Primary Examiner*—Glennon H. Hollrah
*Attorney, Agent, or Firm*—John A. Shedden

[57] ABSTRACT

Solutions containing high concentrations of the n-butyric acid ester and n-octanoic acid ester of bromoxynil (3,5-dibromo-4-hydroxybenzonitrile) or ioxynil (3,5-diiodo-4-hydroxybenzonitrile). Such solutions have crystallization temperatures lower than those of like solutions containing like amounts of any one of such esters alone.

12 Claims, No Drawings

SOLUTIONS OF BROMOXYNIL AND IOXYNIL

FIELD OF THE INVENTION

This invention relates to solutions having high concentrations of esters of bromoxynil and/or ioxynil which are stable at low temperatures.

BACKGROUND OF THE INVENTION

Bromoxynil (3,5-dibromo-4-hydroxybenzonitrile) and ioxynil (3,5-diiodo-4-hydroxybenzonitrile) are well-known herbicides which are commonly used to control annual broadleaf weeds in wheat, barley, oats, rye, flax, and newly-seeded grasses. These materials are sold commercially as solutions of their octanoic acid esters in a suitable hydrocarbon oil in concentrations sufficient to provide 240 g/L of the active 2,6-dihalo-4-cyanophenoxy moiety present therein. However, even at such concentrations, crystallization of these solutions begins to occur at temperatures as high as 20° F. (−7° C.). At higher concentrations, crystallization occurs at even more elevated temperatures. For example, at concentrations of 480 g/L of the active 2,6-dihalo-4-cyanophenoxy moiety, crystallization takes place at about room temperature (20° C.). Since these products are often shipped and marketed during the winter months, they frequently are rendered less effective, or even totally unusable, before they can be used unless precautions are taken to keep them above their crystallization temperatures.

SUMMARY OF THE INVENTION

In accordance with the present invention, it has now been discovered that solutions containing high concentrations of esters of bromoxynil and/or ioxynil can be prepared and rendered stable at temperatures below 0° F. (−18° C.) if the esters employed in these solutions comprise a mixture of both the butyric acid ester and octanoic acid ester thereof.

DETAILED DESCRIPTION OF THE INVENTION

As a result of the present invention, not only is it possible to lower the temperature at which crystallization occurs in solutions containing a given concentration of the active 2,6-dihalo-4-cyanophenoxy moiety present in bromoxynil and ioxynil, but is also possible to increase the concentration of such moiety in solution at a given temperature without crystallization occurring. Consequently, solutions containing a quantity of such moiety equal to that which formerly caused crystallization can now be prepared with significantly lower crystallization temperatures. Likewise, solutions containing two or more times as much of such moiety as formerly present can be prepared at a given temperature before crystallization of the solution begins to occur.

As a result of the present invention, not only has the problem of crystallization of commercial solutions of bromoxynil and ioxynil esters been alleviated, but it is also now possible to significantly increase the concentration of active moiety in such solutions without causing crystallization. Thus, for example, solutions containing in excess of 400 g/L of acting moiety have been found to be free of crystallization at temperatures below 0° F. (−18° C.) when such active moiety is present as both the butyric acid ester and octanoic acid ester of bromoxynil and/or ioxynil. This result is quite surprising inasmuch as the butyric acid ester and the octanoic acid ester of both bromoxynil and ioxynil crystallize at a temperature of about 20° F. (−7° C.) when employed alone at concentrations of about 240 g/L of active moiety, while at concentrations of 480 g/L of active moiety, crystallization occurs at or above room temperature. Because the solutions of the present invention can contain concentrations of active moiety of two or more times that formerly present, the cost of containing and shipping these materials has been considerably reduced.

The esters of bromoxynil and ioxynil which are employed in the solutions of the present invention can be represented by the formula:

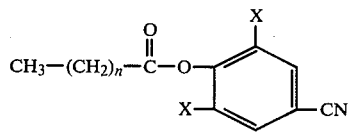

wherein X is a halogen selected from the group consisting of bromine and iodine, and n is an integer having a value of 2 or 6. As aforementioned, the butyric acid ester and octanoic acid ester are employed together, i.e., a mixture of esters is employed wherein n has a value of 2 and 6. Furthermore, it appears to be necessary to employ the normal form of such esters, i.e., the 2,6-dihalo-4-cyanophenyl n-octanoate and the 2,6-dihalo-4-cyanophenyl n-butyrate ester. Thus, other forms of the octanoic acid ester, such as the 2-ethylhexanoic acid ester or the isooctanoic acid ester, are unsuitable as they reduce the activity of the active 2,6-dihalo-4-cyanophenoxy moiety. It has also been found that other esters are not as effective as the octanoic and butanoic acid esters. Thus, replacement of the butyric acid ester with the acetic acid ester is undesirable as such fails to effect a decrease of the crystallization temperature.

The n-butanoic and n-octanoic acid esters of bromoxynil and ioxynil employed in the instant invention can be prepared by conventional techniques by the esterification of 3,5-dibromo-4-hydroxybenzonitrile and 3,5-diiodo-4-hydroxybenzonitrile with n-butanoic acid anhydride and n-octanoic acid anhydride, as disclosed in U.S. Pat. No. 3,397,054. The precursor materials are readily available commercial products.

The crystallization temperature of the solutions of the present invention will vary, of course, with the particular solvent employed, the particular 2,6-dihalo-4-cyanophenoxy moiety present, and the concentration and relative amounts of such moiety which is present as butyric acid ester and octanoic acid ester. Generally, the higher the concentration of such moiety, the higher the crystallization temperature. Commercial solutions should contain at least 200 g/L of the active moiety, and preferably contain at least 400 g/L of such moiety. While solutions having concentrations as high as 800 g/L of such moiety can be prepared, such solutions have comparatively high crystallization temperatures and present storage problems at lower temperatures and present storage problems at lower temperatures. For this reason, concentrations greater than 600 g/L are less desirable.

While the relative amounts of the 2,6-dihalo-4-cyanophenoxy moiety which is present as the butyric acid ester and octanoic acid ester in the solutions of the present invention can vary from a mol ratio of 99:1 to 1:99, such solutions most desirably contain from 20 mol percent to 70 mol percent of such moiety as the butyric acid ester and from 30 mol percent to 80 mol percent as octanoic acid ester. Preferably such solutions contain from 20 mol percent to 60 mol percent of such moiety as the butyric acid ester and from 40 mol percent to 80 mol percent as the octanoic acid ester. Solutions containing such mol ratios generally have a crystallization temperature below about 25° F. (−4° C.), provided the total concentration of the 2,6-dihalo-4-cyanophenoxy moiety does not exceed 500 g/L. Most preferably, such solutions contain from 30 mol percent to 50 mol percent of such moiety as the butyric acid ester and from 50 mol percent to 70 mol percent as the octanoic acid ester.

When the 2,6-dihalo-4-cyanophenoxy moiety is 2,6-dibromo-4-cyanophenoxy, and the solution contains no greater than 600 g/L of such moiety with from 40 mol percent to 50 mol percent thereof present as the butyric acid ester and from 50 mol percent to 60 mol percent thereof present as the octanoic acid ester, the crystallization temperature is generally below about 15° F. (−10° C.). Like solutions having a total concentration of the 2,6-dibromo-4-cyanophenoxy moiety of no greater than 500 g/L generally have a crystallization temperature below about 5° F. (−15° C.), while solutions having a total concentration of such moiety of no greater than 250 g/L generally have a crystallization temperature below about 0° F. (−18° C.).

When the 2,6-dihalo-4-cyanophenoxy moiety is 2,6-diiodo-4-cyanophenoxy, and the solution contains no greater than 600 g/L of such moiety with from 30 mol percent to 40 mol percent thereof present as the butyric acid ester and from 60 mol percent to 70 mol percent thereof present as the octanoic acid ester, the crystallization temperature is generally below about 20° F. (−7° C.). Like solutions having a total concentration of the 2,6-diiodo-4-cyanophenoxy moiety of no greater than 500 g/L generally have a crystallization temperature below about 15° F. (−10° C.), while solutions having a total concentration of such moiety of no greater than about 400 g/L generally have a crystallization temperature below about 0° F. (−18° C.).

The solvent employed for the bromoxynil and and ioxynil esters is generally a hydrocarbon oil, including paraffin oils, aromatic oils and asphaltic oils, although other organic solvents, particularly hydrocarbon solvents, can also be employed. Petroleum-base oils are preferred, although other oils, such as animal and vegetable oils, as well as synthetic oils, are also suitable. In any event, the oil employed most desirably has a high aromatic content (i.e., in excess of about 75 mass percent) because of the greater solubility of bromoxynil esters and ioxynil esters in such solvents. One highly-suitable solvent is HAN* highly-aromatic petroleum solvent, a commercially available petroleum oil containing about 80 volume percent aromatics, about 18 volume percent saturates and about 1 volume percent olefins. Another highly-satisfactory, commercially-available solvent is Getty Oil Company's Aromatic 150, a petroleum oil containing about 98 volume percent aromatics.

*"HAN" is a registered trademark of Exxon Corporation.

The concentrated ester solution of the present invention may be applied to various crops and newly-seeded grasses to control weeds after the addition of water, a liquid fertilizer, or a combination of water and a liquid fertilizer. If desired, other herbicides or materials may be added to the concentrated or diluted solution. Thus, for example, such solutions may contain another herbicide such as 2-methyl-4-chlorophenoxy acetic acid.

The following examples are set forth for purposes of illustration so that those skilled in the art may better understand the invention. It should be understood, however, that they are exemplary only, and should not be construed as limited this invention in any manner.

EXAMPLE 1

Two solutions, each containing 480 g/L of the 2,6-dibromo-4-cyanophenoxy moiety, were prepared. The first solution was prepared by admixing 80.8 grams of 2,6-dibromo-4-cyanophenyl n-octanoate, 7.0 grams of Toximul*S emulsifier, and 34.0 grams of HAN highly-aromatic petroleum solvent. The second solution was prepared by admixing 65.3 grams of 2,6-dibromo-4-cyanophenyl n-butyrate and 7.0 grams of Toximul S emulsifier, and adding a sufficient quantity of HAN highly-aromatic petroleum solvent to bring the mixture to 101 mL at 50° C. (approximately 100 mL at 20° C.). Portions of the two solutions were then mixed together in proportions which provided combined solutions wherein the mol percent of 2,6-dibromo-4-cyanophenoxy moiety derived from the n-octanoate ester and the n-butyrate ester were as set forth in table 1 below. After seeding samples 1 to 5 with 2,6-dibromo-4-cyanophenyl n-octanoate and samples 6 to 9 with 2,6-dibromo-4-cyanophenyl n-butyrate, the samples were cooled for 17.5 hours at a temperature of 21° F. to 25° F. (−4° C. to −6° C.). At the end of this time, samples 1-2 and 9-11 were found to have turned solid, and sample 8 contained some crystalline material. Samples 3-7 did not show any sign of crystallization and were then cooled at 4° F. (−16° C.) for 7 hours. At the end of this time, samples 3, 4 and 7 turned solid, but samples 5 and 6 remained liquid and free of crystals. Table 1 below summarizes the results of the experiment.

*"Toximul" is a registered trademark of Stepan Chemical Company.

| | Mol Percent of 6-Dibromo-4-Cyanophenoxy Moiety Derived From | | State of Sample After | State of Sample After |
|---|---|---|---|---|
| Sample No. | Octanoate Ester | Butyrate Ester | Cooling to 21° F. to 25° F. | Cooling to 4° F. |
| 1 | 100 | 0 | Solid | — |
| 2 | 90 | 10 | Solid | — |
| 3 | 80 | 20 | Liquid | Solid |
| 4 | 70 | 30 | Liquid | Solid |
| 5 | 60 | 40 | Liquid | Liquid |
| 6 | 50 | 50 | Liquid | Liquid |
| 7 | 40 | 60 | Liquid | Solid |
| 8 | 30 | 70 | Crystal Formation | — |
| 9 | 20 | 80 | Solid | — |
| 10 | 10 | 90 | Solid | — |
| 11 | 0 | 100 | Solid | — |

EXAMPLE 2

A solution containing 480 g/L of the 2,6-dibromo-4-cyanophenoxy moiety was prepared by dissolving 2,6-dibromo-4-cyanophenyl n-octanoate and 2,6-dibromo-4-cyanophenyl n-butyrate in HAN highly-aromatic petroleum solvent in proportions wherein the mol ratio of 2,6-dibromo-4-cyanophenoxy moiety derived from the n-octanoate ester and the n-butyrate ester was 55:45. Toximul S emulsifier was also added in an amount equal to 7 g/L.

The solution was found to have a crystallization temperature of −5° F. (−21° C.).

EXAMPLE 3

A solution containing 500 g/L of the 2,6-dibromo-4-cyanophenoxy moiety was prepared as described in Example 2. The solution was found to have a crystallization temperature of 0° F. (−18° C.).

EXAMPLE 4.

A solution containing 600 g/L of the 2,6-dibromo-4-cyanophenoxy moiety was prepared as described in Example 2. The solution was found to have a crystallization temperature of 10° F. (−12° C.).

EXAMPLE 5

A solution containing 400 g/L of the 2,6-diiodo-4-cyanophenoxy moiety was prepared by dissolving 2,6-diiodo-4-cyanophenyl n-octanoate and 2,6-diiodo-4-cyanophenyl n-butyrate in HAN highly-aromatic petroleum solvent in proportions wherein the mol ratio of 2,6-diiodo-4-cyanophenoxy moiety derived from the n-octanoate ester and the n-butyrate ester was 2:1. Toximul S emulsifier was also added in an amount equal to 7 g/L.

The solution was found to be stable at 0° F. (−18° C.)

EXAMPLE 6

A solution containing 400 g/L of the 2,6-diiodo-4-cyanophenoxy moiety wherein the mol ratio of 2,6-diiodo-4-cyanophenoxy moiety derived from the n-octanoate ester and the n-butyrate ester was 3:2 was prepared as described in Example 5. The solution was found to be stable at 0° F. (−18° C.).

EXAMPLE 7

A solution containing 500 g/L of the 2,6-diiodo-4-cyanophenoxy moiety was prepared as described in Example 5. The solution was found to be stable at 20° F. (−7° C.).

EXAMPLE 8

A solution containing 500 g/L of the 2,6-diiodo-4-cyanophenoxy moiety wherein the mol ratio of 2,6-diiodo-4-cyanophenoxy moiety derived from the n-octanoate ester and the n-butyrate ester was 3:2 was prepared as described in Example 5. The solution was found to be stable at 20° F. (31 7° C.).

EXAMPLE 9

A solution containing 600 g/L of the 2,6-diiodo-4-cyanophenoxy moiety was prepared as described in Example 5. The solution was found to be stable at 20° F. (−7° C.).

EXAMPLE 10

A solution containing 300 g/L of the 2,6-dibromo-4-cyanophenoxy moiety and 300 g/L of the 2,6-diiodo-4-cyanophenoxy moiety (1:1 mol ratio) was prepared by dissolving 2,6-dibromo-4-cyanophenyl n-octanoate, 2,6-dibromo-4-cyanophenyl n-butyrate, 2,6-diiodo-4-cyanophenyl n-octanoate, and 2,6-diiodo-4-cyanophenyl n-butyrate in Getty Oil Company's Aromatic 150 petroleum solvent in proportions wherein the mol ratio of total 2,6-dihalo-4-cyanophenoxy moiety derived from n-octanoate esters and n-butyrate esters was 63:36. The mol ratio of 2,6-dibromo-4-cyanophenoxy moiety derived from n-octanoate ester and n-butyrate ester was 2.1, while the mol ratio of 2,6-diiodo-4-cyanophenoxy moiety derived from n-octanoate ester and n-butyrate ester was 3.2. Toximul R-HF emulsifier was also added in an amount equal to 55 g/L.

The solution was found to be stable at 0° F. (−18° C. ).

What is claimed is:

1. A herbicidal solution containing at least one ester selected from the group consisting of 2,6-dibromo-4-cyanophenyl n-octanoate and 2,6-diiodo-4-cyanophenyl n-octanoate and at least one ester selected from the group consisting of 2,6-dibromo-4-cyanophenyl n-butyrate and 2,6-diiodo-4-cyanophenyl n-butyrate wherein from 20 mol. percent to 60 mole percent of such moiety is present as n-butyric acid ester and from 40 mol. percent to 80 mol percent is present as n-octanoic acid ester having from 200 g/L to 800 g/L of the 2,6-dihalo-4-cyanophenoxy moiety dissolved in a high aromatic content, petroleum-base oil, said solution having a crystallization temperature lower than that of a like solution containing a like concentration of 2,6-dihalo-4-cyanophenoxy moiety wherein such moiety is present as only one of 2,6-dihalo-4-cyanophenyl n-octanoate or 2,6-dihalo-4-cyanophenyl n-butyrate.

2. A herbicidal solution as in claim 1 containing from 200 g/L to 600 g/L of 2,6-dihalo-4-cyanophenoxy moiety.

3. A herbicidal solution as in claim 2 containing at least 400 g/L of 2,6-dihalo-4-cyanophenoxy moiety.

4. A herbicidal solution as in claim 1, 2, or 3 wherein the 2,6-dihalo-4-cyanophenoxy moiety is present as 2,6-dibromo-4-cyanophenyl n-octanoate and 2,6-dibromo-4-cyanophenyl n-butyrate.

5. A herbicidal solution as in claim 1, 2 or 3 wherein the 2,6-dihalo-4-cyanophenoxy moiety is present as 2,6-diiodo-4-cyanophenyl n-octanoate and 2,6-diiodo-4-cyanophenyl n-butyrate.

6. A herbicidal as in claim 1, 2 or 3 wherein the 2,6-dihalo-4-cyanophenoxy moiety is present as 2,6-dibromo-4-cyanophenyl n-octanoate, 2,6-diiodo-4-cyanophenyl n-octanoate, 2,6-dibromo-4-cyanophenyl n-butyrate, and 2,6-diiodo-4-cyanophenyl n-butyrate.

7. A herbicidal solution as in claim 1 wherein from 30 mol percent to 50 mol percent of such moiety is present as n-butyric acid ester and from 50 mol percent to 70 mol percent is present as n-octanoic acid ester.

8. A herbicidal solution as in claim 7 containing from 200 g/L to 600 g/L of 2,6-dihalo-4-cyanophenoxy moiety.

9. A herbicidal solution as in claim 8 containing at least 400 g/L of 2,6-dihalo-4-cyanophenoxy moiety.

10. A herbicidal solution as in claim 7, 8 or 9 wherein the 2,6-dihalo-4-cyanophenoxy moiety is present as 2,6-dibromo-4-cyanophenyl n-octanoate and 2,6-dibromo-4-cyanophenyl n-butyrate.

11. A herbicidal solution as in claim 7, 8 or 9 wherein the 2,6-dihalo-4-cyanophenoxy moiety is present as 2,6-diiodo-4-cyanophenyl n-octanoate and 2,6-diiodo-4-cyanophenyl n-butyrate.

12. A herbicidal solution as in claim 7, 8 or 9 wherein the 2,6-dihalo-4-cyanophenoxy moiety is present as 2,6-dibromo-4-cyanophenyl n-octanoate, 2,6-diiodo-4-cyanophenyl n-octanoate, 2,6-dibromo-4-cyanophenyl n-butyrate, and 2,6-diiodo-4-cyanophenyl n-butyrate.

* * * * *